United States Patent [19]

Hesse

[11] Plant 4,985

[45] Feb. 22, 1983

[54] PEACH TREE

[75] Inventor: Claron O. Hesse, Fresno, Calif.

[73] Assignee: The Regents of the University of California, Berkeley, Calif.

[21] Appl. No.: 287,534

[22] Filed: Jul. 27, 1981

[51] Int. Cl.[3] ..... A01H 5/03

[52] U.S. Cl. ..... Plt./42

[58] Field of Search ..... Plt./42

*Primary Examiner*—Robert E. Bagwill

*Attorney, Agent, or Firm*—Roger B. Webster

[57] ABSTRACT

A peach tree which is of medium size and vigor, upright-spreading, and hardy under California conditions; foliated with large, lanceolate leaves having an acuminate apex, a crenate margin, a vigorous petiole of medium length and thickness, and globose, light green, usually opposite glands positioned at base of leaf blade; flowers from buds of medium size and length, pointed, free from stem, and moderately pubescent; the flowers blooming early and being of medium size, non-showy, and having pink-rose petals slightly lighter at base; and is a regular and productive bearer of uniform, medium size, symmetrical, semi-freestone, early-ripening fruit globose in axial aspect and globose to slightly ovate in ventral suture aspect, the fruit having white to cream color flesh, and skin having a yellow ground color substantially blushed with red.

1 Drawing Figure

BACKGROUND OF THE VARIETY

FIELD OF THE INVENTION

In the conduct of an extensive plant breeding program, I originated a substantial number of new and distinct varieties of fruit trees, and which included the herein-claimed variety of peach tree; such plant breeding program having been undertaken at the University of California, Davis, Yolo County, Calif., and particularly in the experimental orchard at such location.

CLASSIFICATION OF THE VARIETY

The present variety of peach tree is embraced by Class 42, Plants, of the U.S. Patent Office Manual of Classification.

PRIOR VARIETIES

Among existing varieties of peach trees which are known to me, and mentioned herein, is the Springtime (U.S. Plant Pat. No. 1,268).

ORIGIN OF THE VARIETY

The present variety of peach tree was originated by me, in the aforesaid experimental orchard, as an open-pollinated seedling of an unnamed peach seedling which bore the identification 4,11-16A.

ASEXUAL REPRODUCTION OF THE VARIETY

Subsequent to its origination by me, the present variety of peach tree was asexually reproduced, on my behalf, by the Kearney Horticultural Field Station located at Parlier, Fresno County, Calif. Such asexual reproduction was accomplished by grafting on suitable peach rootstock, and, in maturity, the reproductions ran true to the original tree of the variety in all respects.

SUMMARY OF THE VARIETY

The present variety of peach tree is of medium size and vigor, upright-spreading, and hardy under California conditions; foliated with large, lanceolate leaves having an acuminate apex, a crenate margin, a vigorous petiole of medium length and thickness, and globose, light green, usually opposite glands positioned at base of leaf blade; flowers from buds of medium size and length, pointed, free from stem, and moderately pubescent; the flowers blooming early and being of medium size, non-showy, and having pink-rose petals slightly lighter at base; and is a regular and productive bearer of uniform, medium size, symmetrical, semi-freestone, early-ripening fruit globose in axial aspect and globose to slightly ovate in ventral suture aspect, the fruit having white to cream color flesh, and skin having a yellow ground color substantially blushed with red.

The present variety of peach tree is particularly characterized by white-flesh, freestone fruit which, in comparison with the fruit of the Springtime, has general resemblance, but — with a relatively short maturation period — ripens approximately three days earlier, is slightly larger in size with a less pronounced tip, and has more red blush color at comparable maturity.

BRIEF DESCRIPTION OF THE DRAWING

The drawing is an illustration, by photographic reproduction in color, of separate leaves and fruit of the variety; one of the fruit being partially cut away to expose the flesh.

DESCRIPTION OF THE VARIETY

The botanical details of this new and distinct variety of peach tree — with color definitions (except those in common color terms) referenced to Maerz and Paul Dictionary of Color (1950 edition) — are as follows:

Tree:

- *Size.*—Medium.
- *Vigor.*—Medium.
- *Growth.*—Upright-spreading.
- *Hardiness.*—Hardy under California conditions.
- *Production.*—Productive.
- *Bearing.*—Regular bearer.

Trunk:

- *Thickness.*—Medium.
- *Surface texture.*—Smooth to medium.

Branches:

- *Size.*—Medium diameter.
- *Surface texture.*—Medium.

*Color.*—Young branches: Brown (8-E-10). Mature branches: Brownish grey (8-A-9). Current season's shoots: Light green (19-H-5) tinged reddish (6-G-4) on exposed surfaces.

*Lenticels.*—Number: Medium. Size: Medium.

Leaves:

*Size.*—Large. Length range — 17.3–19.7 cm. Width range — 4.2–4.8 cm. Leaves measured from midpoint of actively growing shoots.

*Form.*—Lanceolate.

*Apex.*—Acuminate.

*Thickness.*—Medium.

*Texture.*—Relatively smooth.

*Color.*—Top side — Dark green (24-L-9). Under side — Lighter green (21-G-6).

*Margin.*—Crenate. Relatively straight, but occasionally with slight wave.

*Petiole.*—Medium length (10–11 mm. on vigorous growth). Medium thickness.

*Glands.*—Medium size. Globose. Number — range 2–4, occasionally 6. Usually opposite. Positioned at base of leaf blade. Light green on new foliage.

*Stipules.*—Medium size. Narrow. Early deciduous.

Flower buds:

*Hardiness.*—Hardy for California conditions.

*Size.*—Medium.

*Length.*—Medium.

*Form.*—Pointed. Free from stem.

*Pubescence.*—Moderately pubescent.

Flowers:

*Blooming period.*—Early.

*Date of first bloom.*—Feb. 20, 1980.

*Date of full bloom.*—Mar. 4, 1980.

*Size.*—Medium. Diameter range — 26–28 mm., often does not fully open.

*Color of petals.*—Pink-rose (49-H-7). Slightly lighter pink (49-F-4) at base.

*Size of petals.*—Average length — 16 mm. Average width — 10 mm.

*Anthers.*—Light red to orange dorsally.

*Nectaries.*—Greenish.

*Type.*—Non-showy.

*Number.*—Usually 2 per node.

Fruit:

*Maturity when described.*—Commercial harvest maturity — May 19, 1980.

*Harvest period.*—Date of first picking: May 13, 1980. Date of last picking: May 19, 1980.

*Season of maturity.*—Early. About 3 days earlier than Springtime.

*Size.*—Uniform. Medium, but large for an early season freestone peach. Length range — 53–67 mm. Cheek diameter range — 58–68 mm. Suture diameter range — 60–68 mm.

*Form.*—Uniform. Usually symmetrical. Globose in axial aspect. Globose to slightly ovate in ventral suture aspect.

*Suture.*—A shallow, discontinuous line extending from base to apex. Occasionally a slight depression on suture near apex. Occasionally a slight depression beyond the pistil point.

*Ventral surface.*—Rounded. Slightly lipped on right or left side.

*Lips.*—At times slightly unequal.

*Stem cavity.*—Axial aspect — rounded to slightly elongated in suture plane, with suture visible on ventral side only. Length range — 22–27 mm.

Width range — 15–18 mm. Broadly conic, but somewhat shallow. Depth range — 7–9 mm.

*Base.*—Rounded. At right angle to the fruit axis or sloping slightly to the ventral edge.

*Stem.*—Medium length — Range 9–10 mm.

*Apex.*—Rounded.

*Pistil point.*—Apical.

Skin:

*Thickness.*—Medium.

*Texture.*—Medium.

*Tenacity.*—Nearly free when fruit at eating ripe maturity.

*Tendency to crack.*—None.

*Pubescence.*—Moderate. Short. Rolls up when rubbed.

*Color.*—Ground color — Yellow (17-G-1). Blush color — Red (2-J-10) to darker red (5-K-10).

Flesh:

*Color.*—White to cream (18-C-1). Slight red flecking throughout flesh with advanced fruit maturity. Surface of pit cavity: White to cream (10-B-1).

*Amygdalin.*—Scant.

*Juice.*—Abundant.

*Texture.*—Medium. Fine. Melting.

*Fibers.*—Few. Tender.

*Ripens.*—Evenly.

*Aroma.*—Distinct. Very pleasant.

*Flavor.*—Acid to sub-acid. Balanced. Rich.

*Eating quality.*—Good. Outstanding for early season maturity.

Stone:

*Type.*—Semi-free. Adheres to flesh tightly when firm ripe, but will break relatively free when fruit is fully mature. Retains medium size fibers in pit depressions.

*Size.*—Medium. Length range — 35–38 mm. Breadth range — 25–27 mm. Thickness range — 17–18 mm.

*Form.*—Roughly ovoid. Irregular in lateral aspect, with ridges protruding strongly from central dorsal edge.

*Base.*—Oblique toward ventral suture.

*Hilum.*—Generally oval.

*Apex.*—Acute.

*Tip.*—Quite sharp.

*Sides.*—Roughly equal, some variable.

*Surface.*—Regularly furrowed near base and toward apex. Pitted throughout central area in lateral aspect.

*Ridges.*—Rather jagged throughout.

*Pits.*—Variable in shape, usually somewhat angular.

*Ventral edge.*—Medium thickness, with somewhat discontinuous wings. Eroded near base. Converging apically.

*Dorsal edge.*—Narrow, with deep groove from base to above center. Upper dorsal edge heavily eroded from apex down one-third total length of stone.

*Color.*—Buff (10-D-3).

*Tendency to split.*—Slight.

Use: Early shipping; fresh market.

Keeping quality: Medium for season.

Resistance to insects and diseases: Average; no unusual susceptibilities noted.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, characterized by white-flesh, semi-freestone fruit which bears general resemblance to the fruit of the Springtime but ripens approximately three days earlier, is slightly larger in size with a less pronounced tip, and has more red blush color.

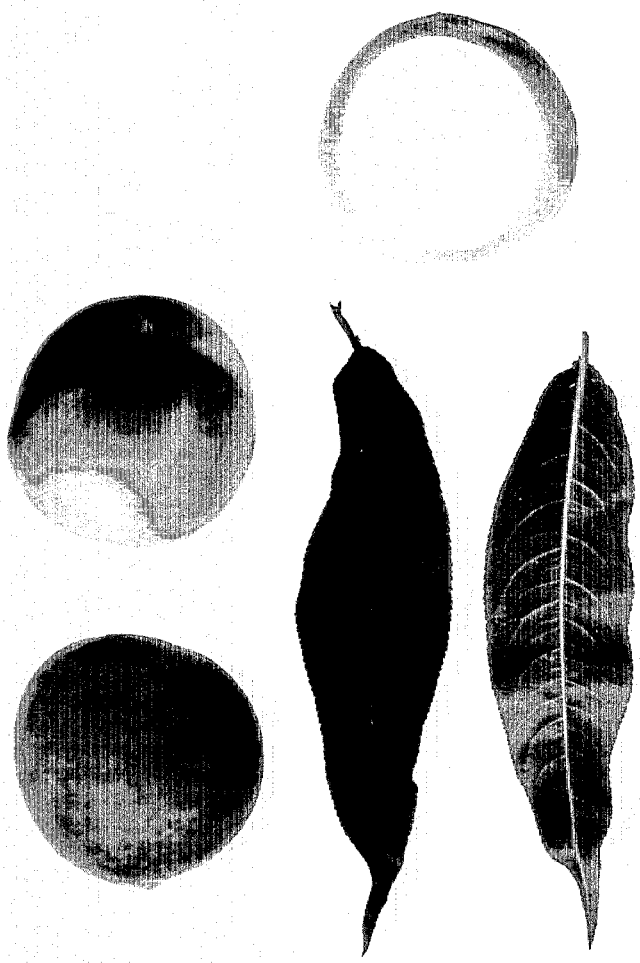

* * * * *